US006737048B2

(12) United States Patent
Abend et al.

(10) Patent No.: US 6,737,048 B2
(45) Date of Patent: May 18, 2004

(54) ANTIPERSPIRANT FORMULATIONS

(75) Inventors: Sven Jorg Willi Max Abend, Bebington (GB); Jean-Philippe Andre Roger Courtois, Bebington (GB); Martin Peter Cropper, Bebington (GB); Neil Robert Fletcher, Bebington (GB); Lynda Grainger, Bebington (GB); Angela Mary Murphy, Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 60 days.

(21) Appl. No.: 10/096,808

(22) Filed: Mar. 13, 2002

(65) Prior Publication Data

US 2003/0064041 A1 Apr. 3, 2003

(30) Foreign Application Priority Data

Mar. 16, 2001 (GB) .............................................. 0106601

(51) Int. Cl.$^7$ ............................. A61K 7/32; A61K 7/34; A61K 7/38; A61K 7/00
(52) U.S. Cl. ............................. 424/65; 424/66; 424/68; 424/400; 424/401; 514/937; 514/938
(58) Field of Search .............................. 424/65, 66, 68, 424/400, 401; 514/937, 938

(56) References Cited

U.S. PATENT DOCUMENTS

| 3,792,068 A | 2/1974 | Luedders et al. ........ 260/429.3 |
| 6,241,976 B1 | 6/2001 | Esser et al. .................. 424/65 |
| 6,287,544 B1 * | 9/2001 | Franklin et al. .............. 424/65 |

FOREIGN PATENT DOCUMENTS

| EP | 6739 | 10/1982 |
| WO | 00/61079 | 10/2000 |
| WO | 00/61080 | 10/2000 |
| WO | 00/61081 | 10/2000 |
| WO | 00/61094 | 10/2000 |
| WO | 00/61096 | 10/2000 |

OTHER PUBLICATIONS

GB Search Report in a GB application GB 0106601.8.
European Search Report in an EP application EP 02 25 1682.

* cited by examiner

*Primary Examiner*—Shelley A. Dodson
(74) *Attorney, Agent, or Firm*—Kevin J. Stein

(57) ABSTRACT

Structured antiperspirant emulsion formulations for topical application to human skin in a cosmetic method for controlling sweat and body odor generation can suffer from problems of impaired sensory properties and impaired efficacy (sweat reduction), which are ameliorated or overcome in structured antiperspirant emulsions in which (%s by weight of the emulsion)

i) the hydrophilic phase comprises 25 to 55%;
ii) the hydrophilic phase contains 0 to 15% polyhydric alcohol;
iii) the emulsifier comprises an alkyl dimethicone copolyol;
iv) the weight ratio of the hydrophilic phase to the emulsifier is selected in the range of at least 60:1
v) the structurant comprises an acylated sugar and
vi) the water-immiscible oil and the structurant are present in a weight ratio of 1.5:1 to 8.5:1.

49 Claims, No Drawings

ANTIPERSPIRANT FORMULATIONS

BACKGROUND TO THE PRESENT INVENTION

The present invention relates to antiperspirant formulations for topical application and in particular to formulations in the form of emulsions.

Humans perspire aqueous sweat through eccrine glands in the course of exercise or as a consequence of emotional stress. In certain areas of the body such as underarm, there is an especially high surface density of eccrine glands which can result in sweat becoming visible, either on the skin itself or by absorption by clothing which comes into contact with the skin in the vicinity of the armpits. In many societies, people wish to avoid the sweat being visible, at least on some areas of the body such as underarm, and accordingly apply topically antiperspirant formulations to those selected areas.

Many antiperspirant formulations which have been developed or/and commercialised comprise an astringent salt, such as an astringent aluminium and/or zirconium salt in a suitable carrier system. Applicators for the formulations can be classified as either contact or non-contact applicators. Non-contact applicators are especially hygienic because there is no contact between the dispenser and the human body in the vicinity of where the formulation is to be applied, but many consumers desire to use contact applicators, especially in North America.

Formulations for contact applicators can themselves be classified into three broad types, based on their physical characteristics. One type comprises lotions, which flow under gravity and are commonly dispensed using a roll-on applicator. A second type comprises a cream or soft solid which commonly have sufficient inherent structure that they either flow very slowly or retain their shape when they are not subjected to pressure, but which flow under pressure. These are commonly dispensed through an applicator comprising a container for the formulation, a perforated cap for the container through which the formulation can flow and a means to pressurise the formulation and urge it towards the perforated cap. A third type comprises a firm stick, which is structured sufficiently to maintain its integrity even when subjected to gentle pressure.

The structured formulations can themselves be further classified into three classes. One class comprises solution formulations. As the name suggests, the active constituent is dissolved in the carrier fluid. In a second class, which comprises suspension formulations, the active constituent is not soluble in the carrier fluid and is present in the form of suspended particles. In the third class, the formulation comprises an emulsion in which droplets of one liquid phase, the internal phase, are dispersed within a continuous second liquid phase, the external phase. Commonly, in respect of antiperspirant formulations, one of the phases is hydrophobic and the other is hydrophilic and the active material is dissolved in the hydrophilic phase. The instant invention relates particularly to the third class, namely structured formulations in the form of such emulsions.

Consumers have regard to many different aspects of antiperspirant products when making their choice from which are products available. These include a choice between contact and non-contact applicators, the physical attributes of an antiperspirant formulation, such as lotion, cream or firm stick and whether it is efficacious. However, they have regard to the aesthetics of the product, such as its appearance and the skin sensations on application of the product, especially when contemplating a repeat purchase. In other words, they take into the account the sensory and visual characteristics of the product. The various different sensory characteristics include whether the formulations feels cool or not on application, whether it feels dry or wet on application, whether it feels sticky, the smoothness with which a contact formulation glides across the skin and whether it feels greasy.

It is a continuing objective of producers of antiperspirant formulations to meet the evolving needs or preferences of their consumers. In that context, the inventors have carried out further investigations into structured antiperspirant emulsions. It will be recognised that emulsions represent comparatively complex systems for delivering an antiperspirant to the skin with inter-relationships between various of the formulation constituents. In common with non-emulsion formulations, there are constraints on the proportions of the various components which can be employed. For example, increasing the proportion any particular constituent reduces the formulation headspace for other constituents, but can also impact upon the efficacy and aesthetics of the product.

However, for emulsions, there is additionally the complication of there being two liquid phases, in both of which their constituents can be varied as well as the volume or weight ratio between the two of them being varied. It will also be recognised that the antiperspirant in an emulsion is commonly a constituent of a disperse hydrophylic phase. The inventors have identified that in order for the antiperspirant active to be effective, the disperse phase should be brought into close contact with the skin in the vicinity of its sweat-producing eccrine glands. The inventors have further found that varying the constituents of one phase may not only change a target functional attribute, but at the same time may also change either the aesthetics or appearance of the product as well, possibly in a manner which is less attractive to consumers. For example, changing the proportion of antiperspirant active solution in the formulation not only can have the effect of changing the efficacy of the product, but can simultaneously change the feel of the product and changing the relative or absolute amounts or the nature of constituents of either phase can alter the appearance of the product. Consequently, the inventors have not only found that there are several relationships between the components of structured emulsions which should be taken into account when seeking to produce an emulsion product, but also that to at least some extent, they can conflict with each other.

It is inherently desirable to produce a product having both acceptable efficacy and acceptable aesthetic attributes. Consequently, when making changes to a formulation in order to improve or optimise the product in one regard, be it sensory properties or efficacy, it is a practical desideratum that such changes do not impair to a significant extent the other properties of the product.

Structured hydrophylic emulsion antiperspirant formulations have been described in a series of recently published PCT applications to Unilever plc et al, including particularly WO00/61079, WO00/61081, WO00/61094 and WO00/61096. In particular, these specifications gave descriptions of various constituents which can be employed in antiperspirant emulsions, including antiperspirant actives, structurants, emulsifiers, constituents of the hydrophylic and non-hydrophylic phases and how to make such emulsions.

Various generalised ranges are given for the components of the structured antiperspirant emulsions and many different structured antiperspirant emulsion formulations are described in the aforementioned Unilever specifications, but there is no direct teaching therein as to which combinations of ingredient proportions have superior and which have inferior efficacy and/or sensory properties. Consequently, the problem remains as to how to select structured antiperspirant emulsions which can provide an improved balance of antiperspirant activity and sensory properties. In other words, the problem remains of how to avoid or ameliorate impairment of sensory properties when improving or maintaining efficacy at the same time as avoiding or ameliorating impairment of efficacy when improving or maintaining sensory properties.

SUMMARY OF THE PRESENT INVENTION

A structured antiperspirant emulsion comprising an hydrophilic phase containing an aluminium and/or zirconium astringent salt dispersed in a continuous oil phase comprising a water-immiscible oil that is structured by a structurant in which the hydrophilic phase comprises from 25 to 55% by weight of the emulsion;

the hydrophilic phase contains a polyhydric alcohol in an amount of from 0 to not more than 15% by weight of the emulsion;

the emulsifier comprises an alkyl dimethicone copolyol;

the weight ratio of the hydrophilic phase to the emulsifier is selected in the range of from at least 60:1 the structurant comprises an acylated sugar and the water-immiscible oil and the structurant are present in a weight ratio of from 1.5:1 to 8.5:1.

By employing, in combination, a proportion of hydrophylic phase that is below a ceiling and containing none or not more than a ceiling proportion of a polyhydric alcohol; selecting a particular class of emulsifier in a specified weight ratio range to the hydrophilic phase, from at least or above a threshold ratio of hydrophylic phase to emulsifier of 60:1; and a specified class of structurants in a selected range of weight ratios to the oil phase which it structures, it is possible to attain, simultaneously, an improved combination of sensory and efficacy properties for the structured antiperspirant product.

DETAILED AND PREFERRED EMBODIMENTS OF THE INVENTION

The present invention relates to structured hydrophylic emulsions containing a specified range of proportions of hydrophylic phase, content of polyhydric alcohol, content of selected class of emulsifier, and content of specified class of structurant in a specified proportion within the emulsion, in order to attain a desired combination of sensory and efficacy properties.

Since the emulsifier constitutes the interface between the hydrophylic and oil phases, it is considered herein as a separate component and not within either phase for the purpose of calculating the weight proportion of either phase.

One of the sensory properties of an antiperspirant composition to which consumers pay particular attention is its stickiness. A number of consumers find it to be an unpleasant sensation if an applicator sticks to the skin during application of the antiperspirant formulation or if, subsequently, the skin sticks together.

Two factors have been identified for emulsions whose oil phase is structured with an acylated sugar. One factor comprises the proportion of polyhydric alcohol in the aqueous phase and the second factor comprises the proportion of the emulsion constituted by internal hydrophylic phase. It can be very desirable to incorporate polyhydric alcohol in the hydrophylic phase of an emulsion, for example as a means to adjust its refractive index or impart moisturising capability, but if too much of the polyhydric alcohol is present, the sensory properties of the emulsion can become progressively impaired. Likewise, although it can be desirable to employ a high internal phase volume, it has been found that this benefit would be achieved at the cost of relatively impaired sensory properties.

As indicated hereinabove, the proportion of internal phase in the instant invention has a ceiling of 55% by weight and the emulsion contains no more than 15% weight of polyhydric alcohol, which in fact will form part of the hydrophylic phase. By employing those two factors in combination, it is possible display good sensory properties, such as good absence of user-perceived stickiness.

However, it is recognised that the employment of a weight proportion of internal hydrophylic phase that is at the lower to middle parts of the practically possible range (maximum or high, commonly about 85%) of internal phase in an emulsion consequently limits the proportion of antiperspirant active which can be incorporated. Accordingly, the inventors sought ways in which the formulation could be controlled so as to improve or is optimise the delivery of the antiperspirant active to the eccrine sweat glands. What they found was that it was of considerable significant to control the weight proportion of the selected emulsifier to the hydrophylic phase. Surprisingly, too much of the selected class of emulsifier is disadvantageous, because it appears to interfere with the delivery of the antiperspirant active to the sweat glands. Accordingly, the instant invention employs a selected range of weight ratios of the emulsifier to the hydrophylic phase. Thirdly, the proportion of structurant is chosen within a specified range that takes into account the consequence of employing a comparatively low internal phase volume.

In many desirable embodiments the proportion of the hydrophylic phase is chosen in the range of from 30 to 50% by weight of the emulsion, often up to 45% by weight and particularly up to 40% by weight. A particularly desirable proportion comprises from 30 to 40% by weight.

The hydrophylic phase can comprise water as the sole hydrophilic liquid. However, additionally, the phase can comprise one or more polyhydric alcohols. Compared with solely employing water as the hydrophylic liquid, their substitution for a fraction of the water permits the refractive index of the phase to be increased, if that is so desired, such as to assist in the formation of a clear product by matching the refractive indexes of the internal and continuous phases.

Preferably, the weight proportion of the polyhydric alcohol is not more than 10% in the emulsion and in a number of beneficial embodiments is at least 1%. In a number of desirable embodiments, the weight ratio of water to polyhydric alcohol in the hydrophylic phase is in the range of from 1:1 to 30:1, and a preferred range comprises from 2:1 to 15:1. Expressed as a weight fraction of the hydrophylic phase, the polyhydric alcohol preferably comprises no more than about ⅔ths.

The polyhydric alcohol is desirably an aliphatic di or trihydric alcohol. Often it contains not more than 6 carbons, and in many instances is selected from propylene glycol, dipropylene glycol, glycerol, and the ether derived from propylene glycol and glycerol. Other polyhydric alcohols which can be contemplated comprise 1,2-hexane diol and 1,3 butane diol.

The emulsions according to the present invention described herein comprise the disperse hydrophobic phase mostly as a minor weight proportion or the remainder at no more than 55% of the emulsion in order for them to enjoy better sensory properties. It is highly desirable for the hydrophylic phase to contain the antiperspirant active salt at a comparatively high concentration. Preferably, the concentration of the antiperspirant active salt is at least 45% and particularly at least 50% by weight of the phase. In at least some preferred embodiments, it is at least 55% by weight. The concentration of the antiperspirant active is commonly less than 70% by weight and in many instances is not greater than 65% by weight.

It is particularly desirable to employ a comparatively high concentration of antiperspirant active in the disperse phase in conjunction with a comparatively low proportion of disperse phase in the emulsion. By a suitable choice of a high concentration of antiperspirant active in the hydrophylic phase and a suitably chosen proportion of hydrophylic phase in the emulsion, it is possible to obtain the benefits of having at least a desired or preferred proportion of antiperspirant active salt in the formulation which can enjoy superior sensory properties compared with formulations containing a similar proportion of antiperspirant salt, but with a higher proportion of disperse phase. For example, in some especially desirable emulsions, the formulations contain from 30 to 40% by weight of the hydrophylic phase, in which the antiperspirant active salt is present in a concentration selected in the range of from 55 to 65% by weight of that disperse phase.

Commonly, the proportion of antiperspirant active salt in many formulations that are preferred herein comprises at least 15% by weight of the emulsion and often up to 30% by weight. In advantageous emulsions herein, the proportion of the antiperspirant salt is at least 18% by weight, and in a number of particularly desirable embodiments, the emulsion contains from 18 to 20% and in others from 20 to 26% by weight of the aluminium and/or zirconium astringent salt.

It has been found that by varying the concentration of antiperspirant active in the hydrophylic phase, and by incorporating to the extent where necessary polyhydric aliphatic alcohol, it is possible to obtain an hydrophylic phase having a refractive index of at least 1.42 such as in the range of 1.42 to 1.45. In a number of embodiments, the refractive index is at least 1.44.

It is an advantage of many emulsions according to the present invention that by the formation of a disperse phase having the antiperspirant salt at a high concentration, it is possible to obtain an elevated refractive index value with the substitution of less polyhydric alcohol for water. Thus, when comparing hydrophylic phases having the same content of antiperspirant active, one being in accordance with the invention and one having a lower concentration of active in the phase, the same refractive index can be attained with less content of polyhydric alcohol. Accordingly, it is possible to bring together the advantages of refractive index adjustment with the benefits of having a lower disperse phase proportion and a lower polyhydric alcohol content.

The antiperspirant active employed herein is an aluminium and/or zirconium astringent salt. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference.

Zirconium actives can usually be represented by the empirical general formula: $ZrO(OH)_{2n-nz}B_z \cdot wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_3CH(NH_2)CO_2H$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

In calculating the proportion of astringent antiperspirant salt in the emulsion or hydrophylic phase thereof, the weight of any water of hydration is normally excluded.

By suitably selecting the weight ratio of disperse phase to emulsifier, it is possible to make the most effective use of the antiperspirant salt, by increasing the extent of sweat reduction attainable at a given weight proportion of antiperspirant active in the emulsion.

Herein, the proportion of the emulsifier is selected in conjunction with the proportion of hydrophylic phase, and in the weight ratio range of the latter to the former of at or above the threshold value of 60:1. In many preferred embodiments, the weight ratio of the disperse phase to the emulsifier is at least 80:1. The ratio of hydrophylic phase to emulsifier is usually not greater than 480:1 and in many instances is up to 360:1, and in some instances up to 180:1. Especially desirable results have been obtained by selecting the ratio in the range of from 100:1 to 150:1, and in a number of advantageous embodiments, the weight ratio of the disperse phase to the emulsifier is selected in the range of from 105:1 to 140:1. In other advantageous formulations, very desirable results have been obtained employing the ratio in the range of from 180:1 to 360:1.

It is particularly advantageous to employ a selected high weight ratio of disperse phase to emulsifier in conjunction with a high concentration of antiperspirant active in that disperse phase, such as a concentration of at least 50% by weight.

As has been described hereinbefore, the instant invention avoids the employment of too much emulsifier, but of course employs an amount effective to form an emulsion. The minimum effective amount will vary, in accordance with the skilled man's understanding, in conjunction with the emulsion-forming process and process conditions employed, such as the rate and extent of shear, and the particular constituents of the hydrophylic and hydrophobic phases. The proportion of emulsifier in the composition is often selected in the range up to 0.75% by weight and in many instances from 0.2 to 0.6% by weight of the composition and in many preferred embodiments is selected in the range of from 0.25 up to 0.4% by weight of the emulsion. In other embodiments, the weight proportion of emulsifier may be up to 0.2%, such as at least 0.1%, and particularly from 0.125% to 0.2%.

The aqueous emulsions according to the invention herein comprise an oil phase which is structured. The oil phase comprises at least one water-immiscible carrier liquid. It will generally be desired that this carrier is liquid (in the absence of structurant) at temperatures of 15° C. and above. It may have some volatility but its vapour pressure will generally be less than 4 kPa (30 mm Hg) at 25° C. so that the material can be referred to as an oil or mixture of oils. Preferably the carrier liquid comprises silicone oils or hydrocarbon oils or a mixture thereof.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa up to 2 kPa at 25° C.

Volatile polyorganosiloxanes can be linear or cyclic or mixtures thereof. Preferred cyclic siloxanes include polydimethylcyclosiloxanes and particularly those containing from 3 to 9 silicon atoms and preferably not more than 7 silicon atoms and most preferably from 4 to 6 silicon atoms, otherwise often referred to as cyclomethicones, including especially pentacycloinethicones. Preferred linear siloxanes include polydimethylsiloxanes containing from 3 to 9 silicon atoms. The volatile siloxanes normally by themselves exhibit viscosities of below $10^{-5}$ $m^2$/sec (10 centistokes), and particularly above $10^{-7}$ $m^2$/sec (0.1 centistokes), the linear siloxanes normally exhibiting a viscosity of below $5 \times 10^{-6}$ $m^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0 to 100% by weight of one or more liquid silicones. Preferably, there is sufficient liquid silicone to provide at least 5% sometimes at least 10%, and on occasions at least 15%, by weight of the whole composition. If silicone oil is used, oil other than volatile silicone preferably comprises at least 20%, desirably at least 30% or at least 40% up to 100% of the weight of the water-immiscible carrier oils. In many instances, when a non-volatile silicone oil is present, its weight ratio to volatile silicone oil is chosen in the range of from 2:1 to 1:40.

Silicon-free hydrophobic oils can be used instead of, or more preferably in addition to liquid silicone oils. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters or liquid aliphatic ethers, but these can be used as only part of the liquid carrier, in total desirably not above 20%, and possibly less than 10% by weight of the blend of water-immiscible oils.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

The liquid aliphatic ethers are desirably derived from at least one fatty alcohol, such as myristyl ether derivatives e.g. PPG-3 myristyl ether or lower alkyl ethers of polygylcols such as PPG-14 butyl ether Such liquid ethers preferably have a melting point of below 20° C.

In many practical emulsions according to the present invention herein, the oil phase comprises a blend of oils including a volatile silicone oil, preferably in a weight proportion of not more than 90% of the blend and an oil other than volatile silicone oil, conveniently a non-volatile oil, suitably providing the balance of the blend. The proportion of non-volatile oil is preferably selected in the range of at least 10% up to 100%, and particularly from 15 to 70% or 85%. In many highly desirable emulsions according to the present invention, non-volatile oils constitute greater than 50% by weight of the blend of oils, such as from 55 to 70% or 70 to 85%. The non-volatile oils can be selected from the classes of oils described hereinabove, and particularly includes non-volatile hydrocarbon oils. A particularly desirable combination comprises pentacyclomethicone and polydecene. The presence of non-volatile oils is of assistance in increasing the refractive index of the oil phase compared with volatile silicone oils.

Herein, the emulsions employ a class of emulsifiers which comprises alkyl dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{22}$ alkyl groups, particularly $C_{12}$ to $C_{18}$. A suitable example comprises cetyl dimethicone copolymer (Abil EM90™ from Th.Goldschmidt).

When greater than 10% by weight of the oil blend comprises other than a volatile silicone oil and the emulsifier comprises a dimethicone copolymer, it is advantageous to select the hydrophylic phase: emulsifier weight ratio in the range of from at least 100:1. In some embodiments, this is conveniently up to 140:1 or even higher, such as from 200:1 to 360:1.

It is especially desirable to employ a comparatively high weight ratio of disperse phase to emulsifier, such as at least 100:1 and particularly at least 105:1, for example in the ranges of ratios indicated hereinabove when the blend of oils in the oil phase contains at least 10% by weight of non-volatile oils, such as from 15% to 70% or 85%. It is furthermore especially desirable to employ such a comparatively high disperse phase:emulsifier weight ratio in conjunction with a comparatively low dispersed phase volume, such as up to 45% by weight of the emulsion and particular 30 to 40% by weight, and particularly when that disperse phase contains the antiperspirant salt at a comparatively high concentration within the phase, such as at least 50% and specially at least 55% by weight.

Herein the oil phase is structured using a structurant. Such a material comprises an acylated sugar (sometimes called an acylated saccharide) which is solid at ambient temperature, eg at 20° C. and can form an homogeneous phase with the carrier oil or blend of oils on being heated to an elevated temperature and mixed together. On subsequent cooling, the structurant re-solidifies, thereby structuring the oil phase.

It is highly desirable herein to employ one or more structurants which are capable of forming a network of fibres. Such structurants are identified and described in greater detail in the above-identified WO00/61079. The fibres formed by such structurants commonly art thin (diameter less than 0.5 μm, often less than 0.2 μm) and are believed to have branches and/or interconnections.

An especially preferred class of saccharide derivative structurants comprises esters with a fatty acid, preferably of 6 to 13 carbon atoms especially 8 to 11 carbon atoms, including nonanoic acid in many instances. A suitable-saccharide derivative comprises acylated maltose. A preferred saccharide derivative comprises acylated cellobiose Preferably, the acylated saccharide is at least 70%, often at least 80% and in many embodiments is at least 90% esterified Herein, percent esterification indicates the average percentage of the total number of hydroxyl groups on the saccharide which have been esterified. For maltose and cellobiose, which each contain 8 hydroxyl groups prior to esterification, such preferred levels of acylation can be attained, conveniently, by a mixture of mainly octaesterification with some heptesterification. One especially preferred structurant comprises cellobiose nonanoate, i.e. cellobiose that has been esterified with nonanoic acid, preferably to at least 70 or 80%. Preferably, at least 75% and often at least 80% of the cellobiose nonanoate comprises the α anomer and the balance comprises the β anomer.

Although in a number of acylated sugars, the sugar So nucleus is acylated by a single fatty acid, e.g. nonanoic acid, in some others, the acyl group at for example the anomeric carbon in the sugar nucleus can be substituted by a different acyl group from that on the other carbon atoms in that nucleus. In such compounds containing ester groups derived from a plurality of different carboxylic acids around the sugar nucleus, such as around the cellobiose nucleus, at least a fraction of the ester residue at the anomeric carbon is different from ester residues of the remaining sugar nucleus carbons. The ester group at the anomeric carbon contains a saturated or unsaturated, linear or branched chain hydrocarbon residue containing from 1 to 31 carbon atoms optionally substituted or an aromatic hydrocarbon residue, optionally substituted or a cycloaliphatic hydrocarbon, optionally substituted of which at least a fraction is different from the ester substituents on non-anomeric carbons, eg different from an octyl residue from esterification with nonanoic acid. At least a major fraction of such acylated sugars which are acylated by two different carboxylic acids are in the form of the β anomer.

Methods for the synthesis of such acylated sugar structurants, where they are not commercially available, can be found in the afore-mentioned referenced specifications, for example WO00/61079, or by a suitable modification to such methods. Modifications can include the substitution of alternative sugars from which derivatives can be formed, and by reducing the ratio of acylating agent to sugar or reducing the reaction rate to allow the reaction to be halted with a fraction of the product not fully esterified and subsequently employing a different acylating agent to increase the extent of acylation.

The oil phase in the invention emulsions herein contain the water-immiscible oil or blend of oils and the structurant in the range of a weight ratios of from 1.5:1 to 8.5:1, particularly in a weight ratio of at least 2:1, and especially from 2.5:1. The weight ratio is often up to 7.5:1, and in many instances not higher than 6:1. It is highly desirable for the concentration of structurant in the emulsion to be at least 6%, and particularly at least 7.5% by weight of the emulsion, and in many instances is not more than 20% by weight of the emulsion.

The benefits of the instant invention are particularly evident when the structurant comprises or consists of a fibre-forming structurant, such as the aforementioned acylated sugars and especially an esterified cellobiose. However, if desired part, eg a minor fraction, of the fibre-forming structurant can be replaced by alternative structurants for an oil blend, such as a wax or a polymeric structurant.

Waxes herein are usually hydrocarbons, silicone polymers, esters of fatty acids or mixtures containing such compounds which are solid at ambient temperature and melt to a mobile liquid at a temperature above 30° C. but generally below 95° C. and preferably in a temperature range of 40° C. to 90° C. They can be produced from natural sources such as plants, eg candelilla, or animals, eg beeswax, or by processing oils, such as hydrogenated castor oil, or can comprise selected compounds therein, either extracted from such waxes or synthesised.

Polymeric structurants include polyamides or siloxane-polymers containing ester, urea, thiourea, or amide groups, as described in one or more of U.S. Pat. Nos. 5,603,925, 5,919,441 or U.S. Pat. No. 6,051,216. Further polymers which can be employed in the hydrophobic phase herein can comprise block copolymers of styrene with an alkylene containing up to 5 carbons, such as especially butadiene or ethylene/butylene. The block copolymers can comprise di-block or tri-block polymers such as those commonly abbreviated to SEB or SEBS copolymers. Commercially available block copolymers can be selected from polymers available under the tradenames Kraton and Transgel. Such copolymers can be employed in weight proportions of up to about 2% and in some instances conveniently from 0.2 to 0.8%.

The invention emulsions can comprise, if desired, one or more optional ingredients.

Optional ingredients in compositions of this invention can include deodorants, for example at a concentration of up to about 10% w/w. Suitable deodorant actives can comprise microbicides, including particularly bactericides, such as chlorinated aromatics, including triclosan, Triclorban™, chlorhexidine and biguanide salts, the latter such as those available under the trade mark Cosmosil™. Yet other highly effective deodorant actives can comprise strong chelators for iron such as diethylene-triaminepentaacetic acid (DTPA) and salts thereof which retard or suppress bacterial re-growth.

Other optional ingredients include wash-off agents, often present in an amount of up to 10% w/w to assist in the removal of the formulation from skin or clothing. Such wash-off agents are typically nonionic surfactants such as ethers containing a $C_8$ to $C_{22}$ alkyl moiety and a hydrophilic moiety which can comprise a polyoxyalkylene group (POE or POP) and/or a polyol. Other ingredients can include skin benefit agents such as glycerol, (already contemplated for incorporation in the hydrophylic phase) and allantoin or lipids, for example in an amount of up to 5%; soluble colorants; skin cooling agents such as menthol and menthol derivatives, often in an amount of up to 2%, all of these percentages being by weight of the emulsion. A commonly employed adjunct is a perfume, which is normally present at a concentration of from 0 to 4% and in many formulations from 0.25 to 2% by weight of the emulsion.

Further optional ingredients include particulate hydrophobic silica, such as in a weight proportion amount of up to 2%, conveniently from 0.2 to 0.7%. The silica is suspended in the oil phase. Desirably, the weight proportion of hydrophobic silica in the oil phase (including any carrier oil and structurant and any other water-immiscible material) is up to 2.5% and in a number of highly desirable formulations, the hydrophobic silica constitutes from 0.5 to 1.5% by weight of the oil phase. Such silica desirable has a low average particle size, often with no more than a minimal weight proportion (eg 0.1%) of above 40 microns diameter, such as is obtainable from fumed silica. The hydrophobic silica herein often has a specific surface area measured by a conventional BET method using nitrogen under standard conditions of at least 100 $m^2/g$, such as from 100 to 350 $m^2/g$, of which many are in the range of from 120 to 250 $m^2/g$. Hydrophobic silicas within a wide range of bulk (free-flowing) density have been found to be desirable, such as from about 35 to about 220 g/l.

Commonly, the silica can be rendered hydrophobic at its surface in a conventional manner, such as by chemical reaction to form substituents of formula —$OSiR_aR_bR_c$ where $R_a$, $R_b$ and $R_c$ represent alkyl groups such as methyl. The measured carbon content (% by weight) of the hydrophobic silica is indicative of the proportion of the silica surface has been rendered hydrophobic, a larger % broadly corresponding to a higher proportion.

A low concentration, such as the concentrations indicated herein, of such hydrophobic silica has been found to improve the sensory properties of the emulsion stick. Furthermore, it has been found that the incorporation of such a small concentration of hydrophobic silica enables those formulations which demonstrate good light transmission in the absence of the silica to retain good transmission in its presence, thereby enabling the superior sensory property to be obtained without significant impairment of clarity.

It can be desirable to employ in the invention emulsions both a block copolymer, such as a SEB or SEBS copolymer together with a hydrophobic silica, each as and in their respective concentrations described hereinbefore. A convenient weight concentration in total of both such ingredients is from 0.5 to 2.0%.

The structured emulsions according to the present invention can be made by a process for the production of an antiperspirant composition comprising, concurrently or in any order, the steps of:

a) incorporating a structurant comprising an acylated sugar into a water-immiscible oil or blend of oils, forming an oil phase in a weight ratio of from 1.5:1 to
b) forming a hydrophylic phase comprising 25 to 55% by weight of the emulsion by dissolving an antiperspirant active in a hydrophylic solvent containing from 0 to not more than 15% by weight of polyhydric alcohol, based on the weight of the emulsion;
c) dispersing the hydrophylic phase within the oil phase in the presence of an alkyl dimethicone copolyol emulsifier in a weight ratio of the hydrophilic phase to the emulsifier in the range of from at least 60:1 and;
d) heating to an elevated temperature at which the structurant is soluble in the oil or blend of oils, followed by
e) introducing the mixture oil phase and disperse hydrophylic phase into a mould which preferably is a dispensing container, and then
f) cooling or permitting the mixture to cool to a temperature at which the oil phase is structured.

Optional ingredient can suitably be incorporated during the preparation of the relevant phase, or may be introduced into the mixture whilst it is mobile.

The emulsions herein are commonly made in the form of firm sticks. As such, they are capable of being dispensed using stick dispensers such as those described in WO0008970.

The invention formulations can be applied to skin in the conventional manner by wiping the sticks across the surface of the skin, and particularly in the axilla. This represents a non-therapeutic method of controlling perspiration and preventing or controlling the generation of body odour, otherwise commonly referred to as a cosmetic method.

Having provided a summary and preferred embodiments of the invention, specific embodiments thereof will now be particularised by way of example only. Variations thereto can be made by the skilled man in the light of the foregoing description.

In the following Examples, the ingredients employed in preparing the formulations were as follows:

| | |
|---|---|
| 1 | volatile silicone oil-DC245 (Dow Corning Inc) |
| 2 | hydrocarbon oil-polydecene-Silkflo 364 (Amoco) |
| 3 | emulsifier-cetyl dimethicone copolyol-Abil EM90 (Th Goldschmidt) |
| 4 | Structurant-cellobiose octananoate (>95% octa) (>95% α anomer) synthesised |
| 5 | antiperspirant astringent salt-Al/Zr tetrahlorohydrex-Rezal 36GP (Reheis) |
| 6 | antiperspirant solution-Al/Zr tetrachlorohydrex-50% w/w in water-Zirconal 50 |
| 7 | Glycerol (Aldrich) |
| 8 | Fragrance |
| 9 | SEB styrene/ethylene/butylene copolymer-Kraton G-1726 |
| 10 | Hydrophobic fumed silica-HDK-H30 |

For use in the Examples and comparisons herein, an acylated sugar structurant was prepared by a process substantially as described in Example 3 of WO00/01081. Cellobiose was acylated to produce an acylated ester in which at least 80% of the product had the α anomeric form, and had been esterified to at least 80% with nonanoate groups.

For use in certain of the Examples, concentrated aqueous solutions of the antiperspirant astringent salt were prepared in a preliminary step by introducing the particulate Al/Zr tetrachlorohydrex (ingredient 5) gradually with stirring into deionised water in a precalculated weight ratio thereto to achieve the desired concentration with gentle heating, optionally also in the presence of glycerol.

The Example Formulations and Comparison Formulations Were Made by the Following General Method:

In a suitably dimensioned flask, the cyclomethicone (volatile silicone oil) was mixed with the other organic oils (if any) and the cetyl dimethicone copolyol which functioned as an emulsifier, and the mixture was heated with gentle stirring to a temperature 5 to 10° C. above the temperature at which the structurant had been found to dissolve (in an earlier test). The structurant, ie an esterified cellobiose, was then added and allowed to dissolve in the blend of oils with stirring whilst the temperature was maintained by heating.

The disperse phase (also referred to as internal phase) comprised the aluminium zirconium active dissolved in water or in a mixture containing the polyhydric alcohol. This disperse phase was pre-heated to the same temperature as the organic oils containing the esterified cellobiose and added slowly to them over a period of one minute while mixing with a Silverson mixer. After addition was complete, the formulation was mixed at higher speed for five minutes. Stirring speed was then reduced for a further one minute, after which the mixture was poured into stick barrels and allowed to cool undisturbed to ambient laboratory temperature.

In many of the Examples, the constituents of the continuous and disperse phases and their proportions were chosen not only to produce an emulsion having the desired sensory and efficacy properties, but also by taking into account their refractive indices, phases refractive index-matched to within 0.01 were obtained.

In the Examples, DPW indicates dispersed phase weight.

EXAMPLE 1

In this Example, the Following Emulsions Were Prepared:

The emulsions were subsequently tested for their sensory properties by application of the test product to standardly washed axillae under controlled conditions by a panel of experienced panellists. Stickiness was assessed by all panellists in two ways. In the first way, the arm was first brought into contact with the body and then lifted to the horizontal three times and how much skin stuck together was assessed. In the second way, the middle three fingers were placed in the axilla and the extent to which the fingers stuck to the axilla skin was assessed. The outcomes from the two methods were aggregated and expressed in Table 1 below.

TABLE 1

| Example ingredients | Ex 1.1 | Ex 1.2 % by weight | Comp A |
|---|---|---|---|
| Hydrocarbon oil 2 | 28.20 | 30.70 | 14.42 |
| Volatile silicone oil 1 | 18.80 | 20.47 | 11.68 |
| Structurant 4 | 15.00 | 15.00 | 2.90 |
| Emulsifier 3 | 0.50 | 0.50 | 1.00 |
| Water | 15.00 | 13.33 | 2.17 |
| Glycerol 7 | 0.00 | 0.00 | 17.84 |
| Antiperspirant solution 6 | 0.00 | 0.00 | 49.99 |
| Antiperspirant 5 | 22.50 | 20.00 | 0.00 |
| DPW % | 37.5 | 33.3 | 70 |
| Stickiness (on application) | good | good | poor |

Poor indicated that a significant fraction of the panellists considered the test product to be sticky. Good indicated that few panellists considered the test product to be sticky.

The results summarized in Table 1 demonstrate that the stickiness felt by the test panel was substantially better for the invention products which had both the DPW and polyhydric alcohol below their respective ceilings compared with the comparison formulation A having a DPW and polyhydric alcohol content above those ceilings.

EXAMPLE 2

In this Example and Comparison, the Emulsions Summarised in Table 2 Were Prepared:

The emulsions were subsequently tested for their antiperspirant efficacy in a standard efficacy test protocol and compared with the efficacy achieved under the same test conditions with a conventional wax-structured suspension antiperspirant stick.

TABLE 2

| Examples and Comparison ingredients | 2.1 | 2.2 | 2.3 % by weight | 2.4 | Comp B |
|---|---|---|---|---|---|
| Volatile silicone oil 1 | 16.29 | 20.18 | | 20.54 | 17.60 |
| Hydrocarbon oil 2 | 24.44 | 30.26 | 50.44 | 30.82 | 26.40 |
| Proportion of non-volatile oil | 60 | 60 | 100 | 60 | 60 |
| Emulsifier 3 | 0.40 | 0.39 | 0.39 | 0.31 | 1.0 |
| Structurant 4 | 5.0 | 7.5 | 7.5 | 15.0 | 5.0 |
| Antiperspirant 5 | | 25.0 | 25.0 | 20.0 | |
| Antiperspirant sol'n 6 | 43.10 | | | | 40.0 |
| Water | | 16.67 | 16.67 | 13.33 | |
| Glycerol 7 | 10.78 | | | | 10.0 |
| DPW % | 53.88 | 41.67 | 41.67 | 33.33 | 50 |
| DPW:emulsifier w/w ratio | 135 | 107 | 107 | 108 | 50 |
| Sweat Reduction | High | High | High | High | Low |

In Table 2, Low indicated that the sweat reduction achieved was markedly lower than that achieved by application of the conventional stick, in the region of ⅔rds or lower.

Medium indicated that the sweat reduction was slightly lower than for the conventional stick, in the region of above ⅔rds to ⅚ths.

High indicated that the sweat reduction achieved was similar to that from the conventional stick, ie above ⅚ths.

The results summarised in Table 2 demonstrate that a substantial and significant improvement in sweat reduction was achieved by controlling the weight ratio of the disperse phase to the emulsifier in the Example formulations which contained a significant fraction of a non-volatile oil to above the threshold of 60:1.

EXAMPLE 3

Further emulsions were made in accordance with the general process at the 3 liter scale and having a composition as summarised in Table 3 below.

TABLE 3

| Examples Ingredients | 3.1 | 3.2 | 3.3 % by weight | 3.4 | 3.5 | 3.6 |
|---|---|---|---|---|---|---|
| Volatile silicone oil 1 | 10.13 | 17.25 | 17.29 | 13.92 | 6.86 | 13.52 |
| Hydrocarbon oil 2 | 40.51 | 25.88 | 25.94 | 20.88 | 27.44 | 20.28 |
| Proportion of non-volatile oil | 80 | 60 | 60 | 60 | 80 | 60 |
| Emulsifier 3 | 0.249 | 0.2 | 0.1 | 0.2 | 0.2 | 0.2 |
| Structurant 4 | 15 | 15 | 15 | 15 | 15 | 15 |
| SEB copolymer 9 | 0.5 | | | | 0.5 | 0.5 |
| H'phobic silica 10 | | | | | | 0.5 |
| Antiperspirant 5 | 20 | 25 | 25 | | | |
| Antiperspirant | | | | 40 | 40 | 40 |

TABLE 3-continued

| Examples solution 6 | 3.1 | 3.2 | 3.3 | 3.4 | 3.5 | 3.6 |
|---|---|---|---|---|---|---|
| Water | 13.61 | 16.67 | 16.67 | | | |
| Glycerol 7 | | | | 10 | 10 | 10 |
| DPW % | 33.61 | 41.67 | 41.67 | 50 | 50 | 50 |
| DPW:emulsifier w/w ratio | 135 | 208 | 417 | 250 | 250 | 250 |
| Sweat Reduction | High | High | High | High | High | High |

From Table 3, it can be seen that emulsions having a high or very high weight ratio of disperse aqueous phase to emulsifier demonstrated high antiperspirant efficacy. Moreover, from Examples 3.1, 3.5 and 3.6, it can be seen significant efficacy was still attained when both a SEB copolymer and a hydrophobic silica was added in order to further alter the sensory properties of the formulation. It was further observed that the amount of emulsifier in Example 3.3 was close to the minimum to produce an emulsion by the method employed.

Further formulations exhibiting a combination of good sensory and antiperspirant efficacy properties can be made by the same process used for and in variation to the emulsions of Example 3. Such variations include, in particular, selecting the weight proportion of carrier oils in the emulsion in the range of 48 to 54%, of which the non-volatile oil or oils preferably contributes from 65 to 77%, the weight proportion of block copolymer is up to 0.7%, the weight proportion of hydrophobic silica is up to 0.7%, the weight proportion of structurant is from 12 to 17%, the weight proportion of glycerol is from 0.5 to 2% and the weight proportion of emulsifier is from 0.14 to 0.18%, giving a ratio of disperse phase to emulsifier of from 180:1 to 290:1. Representative formulations, though not necessarily fully refractive index matched, include those summarised in Table 4 below.

TABLE 4

| Examples Ingredients | 4.1 | 4.2 | 4.3 | 4.4 | 4.5 | 4.6 |
|---|---|---|---|---|---|---|
| | | | parts by weight | | | |
| Volatile silicone oil 1 | 14.2 | 14.6 | 17.4 | 11.15 | 10.4 | 9.85 |
| Hydrocarbon oil 2 | 38.6 | 34.4 | 33.8 | 35.35 | 37.7 | 39.41 |
| Proportion of non-volatile oil | 73 | 70 | 66 | 76 | 78 | 80 |
| Emulsifier 3 | 0.17 | 0.18 | 0.16 | 0.14 | 0.15 | 0.16 |
| Structurant 4 | 15.5 | 13.7 | 12.6 | 12.18 | 14.67 | 15.56 |
| SEB copolymer 9 | | 0.5 | 0.24 | 0.35 | 0.4 | |
| H'phobic silica 10 | 0.27 | 0.5 | | 0.45 | 0.6 | 1.0 |
| Fragrance | 0.65 | 0.5 | 0.5 | 0.55 | 0.8 | 0.75 |
| Antiperspirant solution 6 | 17.9 | 20.6 | 21 | 23.14 | 20.4 | 20.17 |
| Water | 11.45 | 13.9 | 14.3 | 15.1 | 13.5 | 12.6 |
| Glycerol 7 | 1.26 | 1.12 | | 1.59 | 1.39 | 0.84 |
| DPW % | 30.61 | 35.62 | 35.3 | 39.83 | 35.29 | 33.61 |
| DPW:emulsifier w/w ratio | 180 | 198 | 221 | 285 | 235 | 210 |

Example 4.6 was varied by substituting a number of other HDK grades of hydrophobic silica available from Wacker Chemie, viz 4.6a, H2000; 4.6b H18; and 4.6c H15, the product details of which were available in February 2002 via their website www.wacker.com.

The emulsions 4.1 to 4.6 and the variants of 4.6 were found to exhibit superior sensory properties when applied topically to human skin when compared with the same formulation containing neither block copolymer nor hydrophobic silica. Variant 4.6a having a moderate specific surface area of about 140 m2/g and a high bulk density (200 g/l approx.) was particularly impressive as regards product clarity.

We claim:

1. A structured antiperspirant emulsion comprising an hydrophilic phase containing water and an aluminium and/or zirconium astringent salt dispersed in a continuous oil phase comprising a water-immiscible oil that is structured by a structurant in which
   i) the hydrophilic phase comprises from 25 to 55% by weight of the emulsion;
   ii) the hydrophilic phase contains a polyhydric alcohol in an amount of from 0 to not more than 15% by weight of the emulsion;
   iii) the emulsifier comprises an alkyl dimethicone copolyol;
   iv) the weight ratio of the hydrophilic phase to the emulsifier is selected in the range of from at least 60:1;
   v) the structurant comprises an acylated sugar and
   vi) the water-immiscible oil and the structurant are present in a weight ratio of from 1.5:1 to 8.5:1.

2. An antiperspirant emulsion according to claim 1 in which the hydrophylic phase contains at least 1% by weight of a polyhydric alcohol.

3. An antiperspirant emulsion according to claim 1 in which the hydrophylic phase contains the water in a weight ratio to the polyhydric alcohol of from 1:1 to 30:1.

4. An antiperspirant emulsion according to claim 3 in which the hydrophylic phase contains the water in a weight ratio to the polyhydric alcohol of from 2:1 to 15:1.

5. An antiperspirant emulsion according to claim 1 in which the emulsion contains from 8 to 19% by weight of water.

6. An antiperspirant emulsion according to claim 1 in which the polyhydric alcohol comprises an aliphatic di or trihydric alcohol.

7. An antiperspirant emulsion according to claim 6 in which the aliphatic di or trihydric alcohol comprises propylene glycol, dipropylene glycol, glycerol or a propylene glycol/glycerol ether or any mixture of two or more thereof.

8. An antiperspirant composition according to claim 7 which contains up to 5% by weight glycerol.

9. An antiperspirant emulsion according to claim 1 in which the proportion of the hydrophylic phase in the emulsion is selected in the range of from 30 to 50% by weight.

10. An antiperspirant emulsion according to claim 9 in which the proportion of hydrophylic phase in the emulsion is selected in the range of at from 30 to 40% by weight.

11. An antiperspirant emulsion according to claim 1 in which the weight proportion of the aluminium and/or zirconium astringent salt in the emulsion is selected within the range of at least 15%.

12. An antiperspirant emulsion according to claim 1 in which the weight proportion of the aluminium and/or zirconium astringent salt in the emulsion is selected within the range of from 18 to 26%.

13. An antiperspirant emulsion according to claim 1 in which the concentration of the aluminium and/or zirconium astringent salt in the hydrophylic phase is selected in the range of at least 45% by weight.

14. An antiperspirant emulsion according to claim 13 in which the concentration of the aluminium and/or zirconium astringent salt in the hydrophylic phase is selected in the range of from 52.5% to 65% by weight of the hydrophylic phase.

15. An antiperspirant emulsion according to claim 1 in which the hydrophylic phase has a refractive index of at least 1.42.

16. An antiperspirant emulsion according to claim 15 in which the hydrophylic phase has a refractive index of at least 1.44.

17. An antiperspirant emulsion according to claim 1 in which the hydrophylic phase is present in a weight ratio to the emulsifier of up to 480:1.

18. An antiperspirant emulsion according to claim 17 in which the hydrophylic phase is present in a weight ratio to the emulsifier of up to 320:1.

19. An antiperspirant emulsion according to claim 1 in which the hydrophylic phase is present in a weight ratio to the emulsifier of at least 100:1.

20. An antiperspirant emulsion according to claim 1 in which the hydrophylic phase is present in a weight ratio to the emulsifier of up to 180:1.

21. An antiperspirant emulsion according to claim 20 in which the emulsifier is present in a weight ratio to the hydrophylic phase of from 1:100 to 1:150.

22. An antiperspirant emulsion according to claim 21 in which the emulsifier is present in a weight ratio to the hydrophylic phase of from 1:105 to 1:140.

23. An antiperspirant emulsion according to claim 19 in which the emulsifier is present in a weight ratio to the hydrophylic phase of from 1:180 to 1:300.

24. An antiperspirant emulsion according to claim 17 in which the concentration of the aluminium and/or zirconium astringent salt in the hydrophylic phase is selected in the range of at least 45% by weight.

25. An antiperspirant emulsion according to claim 1 which contains the emulsifier in an amount selected within the range of at least 0.1% by weight of the emulsion.

26. An antiperspirant emulsion according to claim 25 which contains the emulsifier in an amount selected within the range of from 0.2 to 0.6% by weight of the emulsion.

27. An antiperspirant emulsion according to claim 26 which contains the emulsifier in an amount selected within the range of from 0.25 to 0.4% by weight of the emulsion.

28. An antiperspirant emulsion according to claim 25 in which it contains an the emulsifier in an amount selected within the range of from 0.125 to 0.2% by weight of the emulsion.

29. An antiperspirant emulsion according to claim 1 in which the oil phase comprises a blend of a silicone fluid and/or a hydrocarbon fluid.

30. An antiperspirant emulsion according to claim 1 in which not more that 90% by weight of water-immiscible oils in the oil phase constitute volatile silicone oils and the balance of water-immiscible oils constitutes a non-volatile water-immiscible oil.

31. An antiperspirant emulsion according to claim 30 in which the proportion of non-volatile oil in the oil phase is up to 85% by weight of the total weight of volatile and non-volatile water-immiscible oils.

32. An antiperspirant emulsion according to claim 31 in which the proportion of non-volatile oil in the oil phase is greater than 50% up to 70% or from 70 to 85% by weight of the total weight of volatile and non-volatile water-immiscible oils.

33. An antiperspirant emulsion according to claim 1 in which the oil phase comprises a mixture of a pentacyclomethicone and polydecene.

34. An antiperspirant emulsion according to claim 1 in which the hydrophylic phase and the oil phase have a refractive index matched to within 0.01 units.

35. An antiperspirant emulsion according to claim 1 in which the water-immiscible oil is present in a weight ratio to the structurant of from 2.5 to 6:1.

36. An antiperspirant emulsion according to claim 1 in which the structurant comprises from 7.5 to 20% by weight of the emulsion.

37. An antiperspirant emulsion according to claim 1 in which the structurant for the oil phase comprises an acylated cellobiose.

38. An antiperspirant emulsion according to claim 37 in which the acylated cellobiose comprises at least 80% by weight a cellobiose and is acylated to at least 80%.

39. An antiperspirant emulsion according to claim 38 in which the acylated cellobiose is cellobiose nonanoate.

40. An antiperspirant emulsion according to claim 1 which additionally contains up to 2% by weight of a particulate hydrophobic silica.

41. An antiperspirant emulsion according to claim 40 in which the particulate hydrophobic silica constitutes from 0.5 to 1.5% by weight of the oil phase.

42. An antiperspirant composition according to claim 1 which additionally contains up to 2% by weight of a block copolymer.

43. An antiperspirant emulsion according to claim 42 in which the block copolymer is an SEB or SEBS copoymer.

44. An antiperspirant emulsion according to claim 1 which additionally contains up to 2.0% by weight in total of a particulate hydrophobic silica and a block copolymer.

45. A structured antiperspirant emulsion comprising an hydrophilic phase containing water and an aluminium and/or zirconium astringent salt dispersed in a continuous oil phase comprising a water-immiscible oil that is structured by a structurant in which
   i) the hydrophilic phase comprises from 25 to 55% by weight of the emulsion;
   ii) the aluminium and/or zirconium astringent salt is present in the hydrophylic phase at a concentration of at least 45% by weight of the phase:
   iii) the hydrophilic phase contains glycerol in an amount of from 0 to 5% by weight of the emulsion;
   iv) the emulsifier comprises an alkyl dimethicone copolyol, present in an amount of from 0.1 to 0.6% by weight of the emulsion;
   v) the weight ratio of the hydrophilic phase to the emulsifier is selected in the range of from 100:1 to 300:1;
   vi) the structurant comprises an acylated cellobiose and
   vii) the water-immiscible oil and the structurant are present in a weight ratio of from 2.5:1 to 7.5:1.

46. An antiperspirant emulsion according to claim 45 which contains up to 1.5% by weight in total of a particulate hydrophobic silica and a block copolymer.

47. A process for the production of an antiperspirant composition comprising, concurrently or in any order, the steps of
   incorporating a structurant comprising an acylated sugar into a water-immiscible oil or blend of oils, forming an oil phase in a weight ratio of from 1.5:1 to 7.5:
   forming a hydrophylic phase comprising 25 to 55% by weight of the emulsion by dissolving an antiperspirant active in a hydrophylic solvent containing from 0 to not more than 15% by weight of polyhydric alcohol, based on the weight of the emulsion;
   dispersing the hydrophylic phase within the oil phase in the presence of an alkyl dimethicone copolyol emulsifier in a weight ratio of the hydrophilic phase to the emulsifier in the range of at least 60:1;
   heating to an elevated temperature at which the structurant is soluble in the oil or blend of oils, followed by
   introducing the mixture oil phase and disperse hydrophylic phase into a mould which preferably is a dispensing container, and then cooling or permitting the mixture to cool to a temperature at which the oil phase is structured.

48. A cosmetic method for preventing or reducing perspiration on human skin comprising topically applying to the skin a A structured antiperspirant emulsion comprising an hydrophilic phase containing water and an aluminium and/or zirconium astringent salt dispersed in a continuous oil phase comprising a water-immiscible oil that is structured by a structurant in which i) the hydrophilic phase comprises from 25 to 55% by weight of the emulsion;

ii) the hydrophilic phase contains a polyhydric alcohol in an amount of from 0 to not more than 15% by weight of the emulsion;

iii) the emulsifier comprises an alkyl dimethicone copolyol;

iv) the weight ratio of the hydrophilic phase to the emulsifier is selected in the range of from at least 60:1;

v) the structurant comprises an acylated sugar and vi) the water-immiscible oil and the structurant are present in a weight ratio of from 1.5:1 to 8.5:1.

49. A cosmetic method according to claim 48 in which:

the aluminium and/or zirconium astringent salt is present in the hydrophylic phase at a concentration of at least 45% by weight of the phase:

the hydrophilic phase contains glycerol in an amount of from 0 to 5% by weight of the emulsion;

the emulsifier comprises an alkyl dimethicone copolyol, present in an amount of from 0.1 to 0.6% by weight of the emulsion;

the weight ratio of the hydrophilic phase to the emulsifier is selected in the range of from 100:1 to 300:1;

the structurant comprises an acylated cellobiose and the water-immiscible oil and the structurant are present in a weight ratio of from 2.5:1 to 7.5:1.

* * * * *